(12) United States Patent
Rochat

(10) Patent No.: US 7,351,059 B2
(45) Date of Patent: Apr. 1, 2008

(54) PROCESS FOR TREATING A SURFACE

(75) Inventor: Pierre Rochat, Geneva (CH)

(73) Assignee: Exa SA (CH)

( * ) Notice: Subject to any disclaimer, the term of this patent is extended or adjusted under 35 U.S.C. 154(b) by 0 days.

(21) Appl. No.: 10/502,241

(22) PCT Filed: Sep. 24, 2002

(86) PCT No.: PCT/EP02/10692

§ 371 (c)(1),
(2), (4) Date: Jan. 28, 2005

(87) PCT Pub. No.: WO03/061908

PCT Pub. Date: Jul. 31, 2003

(65) Prior Publication Data
US 2005/0123572 A1    Jun. 9, 2005

(30) Foreign Application Priority Data
Jan. 24, 2002   (IE) ................. S2002/0038

(51) Int. Cl.
A61C 3/02     (2006.01)
B24B 1/00     (2006.01)
B24C 1/00     (2006.01)

(52) U.S. Cl. .............. 433/88; 451/38; 451/39

(58) Field of Classification Search ........... 433/216, 433/229, 88, 80; 424/401, 489; 451/36–40, 451/90
See application file for complete search history.

(56) References Cited

U.S. PATENT DOCUMENTS

| | | | | |
|---|---|---|---|---|
| 3,090,166 A | * | 5/1963 | Straub | 451/39 |
| 3,491,563 A | * | 1/1970 | Alonso | 72/53 |
| 3,559,344 A | * | 2/1971 | Peterson | 451/38 |
| 3,864,471 A | * | 2/1975 | King et al. | 424/52 |
| 4,369,605 A | * | 1/1983 | Opersteny et al. | 451/38 |
| 5,199,229 A | * | 4/1993 | Herold et al. | 451/102 |
| 5,203,698 A | * | 4/1993 | Blake et al. | 433/88 |
| 5,334,019 A | * | 8/1994 | Goldsmith et al. | 433/88 |
| 5,356,291 A | * | 10/1994 | Darnell | 433/216 |
| 5,810,587 A | * | 9/1998 | Bruns et al. | 433/88 |
| 5,827,114 A | * | 10/1998 | Yam et al. | 451/75 |
| 5,865,620 A | * | 2/1999 | Kutsch | 433/88 |
| 5,984,678 A | * | 11/1999 | Bruns et al. | 433/88 |

(Continued)

Primary Examiner—John J Wilson
(74) Attorney, Agent, or Firm—Andrus, Sceales, Starke & Sawall, LLP

(57) ABSTRACT

A process for treating a surface (2) to clean or otherwise treat the surface (2) comprises a step of contacting the surface (2) with a particulate treating agent such that at least some of the particles (1) roll along at least a portion of the surface (2), wherein an angle of incidence of the particles (1) and the surface is between 0° and 60°. The particles (1) are dimensioned to effect a rolling movement along the surface (2). The treating agent is substantially non-aqueous. The particles (1) comprise a precipitate or agglomerate of an insoluble alkali metal carbonate. The process comprises a blasting operation or a manual application. The use of the process of the invention in dental applications such as teeth whitening and plaque removal, treating bone, and skin exfoliation, is also disclosed. Also disclosed is a treating agent which comprises a plurality of particles (1), the particles (1) being dimensioned to effect a rolling movement along a surface (2), wherein the treating agent is substantially non-aqueous.

4 Claims, 1 Drawing Sheet

U.S. PATENT DOCUMENTS 6,273,788 B1 * 8/2001 Shaw .......................... 451/38
6,273,789 B1 * 8/2001 LaSalle et al. ................ 451/38
6,485,304 B2 * 11/2002 Beerstecher et al. .......... 433/88

* cited by examiner

PROCESS FOR TREATING A SURFACE

TECHNICAL FIELD

The invention relates to a process for treating a surface to clean or otherwise treat the surface, the process being of the type which employs a treating agent comprising a plurality of particles.

BACKGROUND

Cleaning of the surfaces of various types of equipment and structures is often desirable. Numerous processes and cleaning agents are known in the art. The choice of process and agent depends to a great extent on the coating to be removed and on the substrate. In addition, the working conditions and the environmental effects of the process and agent used are becoming increasingly important factors when selecting an optimal cleaning technique.

Sand blasting and other abrasive techniques are quite applicable on hard substrates, but require special arrangements to meet the specification related to environment and working conditions.

Less hard and durable substrates like aluminium, wood and composite materials require processes and cleaning agents which do not cause mechanical or chemical damage to the surface of the substrate.

International Patent Application No PCT/NO93/00137 in the name of Norsk Hydro A. S discloses a wet blasting process which employs an aqueous slurry of precipitated, non-soluble, calcium carbonate. The use of such aqueous wet blasting agents has a number of disadvantages. The aqueous blasting slurries have a tendency to freeze when used in countries where severe winters are encountered. Further, the presence of water in blasting slurries can have the effect of contributing to erosion of the surface being cleaned. This problem is particularly acute when the surface being cleaned forms part of a structure or building. Moreover, the use of aqueous blasting slurries to treat surfaces having electrical components can be particularly hazardous and can cause corrosion.

It is an object of the invention to overcome at least some of the above disadvantages.

STATEMENTS OF INVENTION

According to the invention, there is provided a process for treating a surface to clean or otherwise treat the surface, the process being of the type which employs a treating agent comprising a plurality of particles, the process comprising the step of contacting the surface with the treating agent such that at least some of the particles roll along at least a portion of the surface, wherein an angle of incidence of the particles and the surface is between 0° and 60°, wherein the particles are dimensioned to effect a rolling movement along the surface, and wherein the treating agent is preferably substantially non-aqueous.

In this specification, the term "substantially non-aqueous" as applied to treating agents should be understood as meaning treating agents having less than 5% water. A minimal amount of water is often included in the treating agent to minimise the production of dust.

In one embodiment of the invention, the treating agent comprises less than 5% water, suitably less than 4% water, typically less than 3% water, preferably less than 2% water, and ideally less than 1% water.

When the projected particle impacts the substrate at a low angle of incidence it rolls along the surface, rubbing and absorbing the coating from the surface.

In one embodiment of the invention, the treating agent includes an non-aqueous solvent such as, for example, an alcohol.

In a preferred embodiment of the invention, the particles are non-crystalline.

In one preferred embodiment of the invention, the particles comprise a precipitate or agglomerate of an insoluble alkali metal salt. Typically, the salt is a carbonate. Suitably the metal is calcium or magnesium.

Preferably, the particles are generally round. In this specification the term "generally round" as applied to particles should be understood to mean any shape which of particle which enables the particle to easily assume a rolling motion when moved along a surface. As such, while the term is primarily intended to refer to spherical particles, it is not intended to exclude other types of spheroids such as spheres having an oblong or elliptical shape. Typically, the particles will have an irregular surface configuration.

Ideally, the particles are relatively soft. Generally, the particles have an average hardness of less than 10 Mohs, typically less than 8 Mohs, and preferably less than 6 Mohs. Typically, the particles will have an average hardness of at least 1 Mohs, and preferably of at least 2 Mohs. In a preferred embodiment of the invention, the particles will have an average hardness of about 3 Mohs. Typically, the particles have an average maximum diameter of between 30 and 1000 microns.

The process of the invention may be a blasting operation or a manual rubbing operation.

When the process of the invention is a blasting operation, various means of blasting are envisaged, such as for example, mechanical projection (i.e. centrifugal particle acceleration), pneumatic particle projection and electrostatic particle projection. A mechanical particle projecting device which is suitable for carrying out the process of the invention is described in published International Patent Application No PCT/EP00/09960. Generally speaking, dry blasting is envisaged. However, in certain circumstances wet blasting may be appropriate whereby a wet component of the treating agent is non-aqueous. Such a wet component may be a non-aqueous solvent such as, for example, an alcohol.

When the process of the invention involves manual projection of the particles along the surface, the particles may be rubbed along the surface using a cloth, by hand, or by any other means such as, for example, a mechanical polishing, brushing or rubbing apparatus or the like.

The invention also relates to the use of the process of the invention in dental applications such as teeth whitening, plaque removal and general cleaning or polishing of the teeth, buccal cavity, and prosthetic parts such as crowns, bridges and complete or partial dentures. As such, the process may involve either blast application using some form of particle accelerator, or manual application, of the treating agent. Manual application includes conventional brushing, rubbing, polishing or the like.

The invention also relates to the use of the process of the invention in treating bone.

The invention also relates to the use of the process of the invention in cosmetic application. Thus, the process may be employed to remove skin in, for example, an exfoliating application.

The invention also relates to the use of the process of the invention in treating automobiles, bikes, aeroplanes, boats, casting dies, machines and parts thereof. In addition, the process may be utilised in treating and/or maintaining equipment in petrochemical, chemical and food production facilities.

The invention also relates to an agent for treating a surface to clean or otherwise treat the surface, the agent being of the type comprising a plurality of particles, the particles comprising a precipitate or agglomerate of an insoluble alkali metal salt, wherein the treating agent is preferably substantially non-aqueous. Typically, the salt is a carbonate. Suitably the metal is calcium or magnesium.

The invention also relates to the use of a treating agent of the invention in dental applications.

The invention also relates to the use of a treating agent of the invention to treat bone.

The invention also relates to the use of a treating agent of the invention in cosmetic applications, such as, for example, to remove skin.

The use of substantially non-aqueous treating agents has a number of advantages. Aqueous treating agents such as blasting slurries have a tendency to freeze when used in countries where severe winters are encountered. Further, the presence of water in blasting slurries can have the effect of contributing to erosion of the surface being cleaned. This problem is particularly acute when the surface being cleaned forms part of a structure or building. Moreover, the use of aqueous blasting slurries to treat surfaces having electrical components can be particularly hazardous due to corrosion. Use of the process and treating agents of the invention obviates these problems.

Use of the process of the invention has the effect of removing coatings without damaging the surface of the substrate. It should also be possible to clean complete structures and equipment having complex geometrical configurations such as valves, bridges, bearings, ballbearings etc having parts which are difficult to access with conventional cleaning equipment or conventional blasting jets.

After having cleaned or otherwise treated the substrate according to the process of the invention the treating agent is easily removed together with the removed coating. The cleaning agent itself is environmentally acceptable.

BRIEF DESCRIPTION OF THE DRAWINGS

The invention will be more clearly understood from the following description of some embodiments thereof, given by way of example only, with reference to the following figures in which.

DETAILED DESCRIPTION

The present invention has been found to be effective at removing various types of coatings from substrates having hardness from that of steel to wood (or even softer materials) without causing damage to the subtrates surface. The treating agent can easily be removed by flushing with water or compressed air. The person carrying out the cleaning process is not exposed to any harm and the agent is acceptable from an environmental point of view. The agent is also available in desired qualities, particle size, hardness etc.

Figure 1:
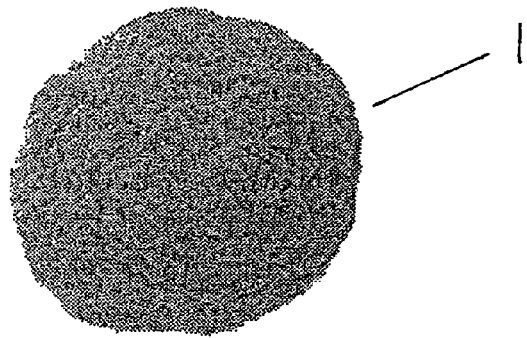
FIG. 1 is an illustration of a particle of a treating agent according to the invention.

Referring to the drawings, and initially to FIG. 1, there is illustrated a particle, indicated generally by the reference numeral 1, which is used in the process of the invention. The particle is a particle of precipitated calcium carbonate and has a generally round, and slightly irregular, shape and a rough, irregular, surface configuration.

Figure 2:
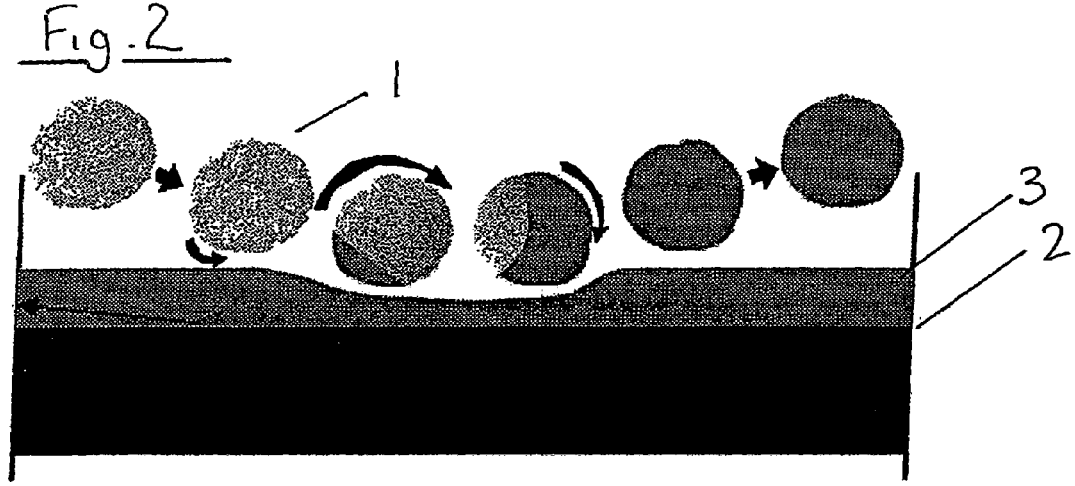
FIG. 2 illustrates the process of the invention.

Referring to FIG. 2, the process of the invention is illustrated in which the particle 1 is projected towards a surface 2 having a coating 3 to be removed. Due to the low angle of incidence of the particle 1 and the surface 2, and the generally round shape of the particle 1, upon impact the particle 1 rolls along the surface, rubbing the surface and absorbing the coating 3 onto a surface of the particle. This has the net effect of removing the coating from the surface without causing any damage to the surface.

EXAMPLE 1

Method of production of particles.

Production of insoluble particles CaCO3 is carried out by providing free $Ca^{++}$ in a liquid with a PH over 7 by dissolving calcium oxide in water.

Addition of $CO_2$ results in the precipitation $CaCO_3$.

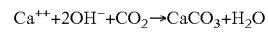
$$Ca^{++}+2OH^-+CO_2 \rightarrow CaCO_3+H_2O$$

Various other methods of production of particles forming part of treating agents according to the invention have been investigated using various types of substrates including plastic, metal and polymer. Examples of these methods include:

Chemical

There are numerous chemical methods for producing spherical powders. Generally, chemical methods result in very fine powder particle sizes. Such methods include Sol Gel, chemical precipitation, Reaction, reduction (hydrogen in an autoclave to reduce metal salts to the metal), decomposition (eg metal carbonyls) and Electrolysis.

Spray Drying

This is the most widely used industrial process involving particle formation and drying. It is highly suited for the continuous production of dry solids in either powder, granulate or agglomerate form from liquid feedstocks as solutions, emulsions and pumpable suspensions.

Agglomeration

The most common method of agglomeration is where the constituents are physically mixed together with an organic binder. The solvent is then driven off and the resultant material sized. The binder should be burnt off during spraying. This process is used in the manufacture of NiAl, AlSi or polyester powders. The most common method of agglomeration is where the constituents are physically mixed together with an organic binder. The solvent is then driven off and the resultant material sized. The binder should be burnt off during spraying. This process is used in the manufacture of NiAl, AlSi-polyester powders. The use of spray drying has become another common method for the agglomeration of powders. Here, a slurry is formed with the constituents and this is then fed into a rotary spray head. Here, the slurry forms an atomised cloud which is solidified by an opposing warm air stream to produce a powder. This method is used for ceramics such as zirconia and cermets such as WC-cobalt. The powder is largely spherical but in the as spray dried state can be porous and friable. The material is often densified and stabilised by sintering and/or spray densification.

There are also methods of mechanical agglomeration (eg the Hosakawa method) where for example a hard constituent is mechanically driven into a softer matrix particle to form a composite powder. Indeed, simple ball grinding can be used to mechanically alloy two or more constituents together. Although sintering can be used as part of the spray drying process it can also be used alone as a method to manufacture powders. The constituents are mixed together and heated to get some solid state diffusion going and then the resultant product is crushed. A number of repeated cycles can be used to promote further alloying in which case the powder is called a "reacted" powder.

Atomisation

There are a number of atomisation techniques which all rely on the production of a molten pool as the source. Atomisation methods include Rotating Electrode, Vibrating Electrode (arc), centrifugal (from a melt) and Rapid Solidification (eg aluminium ribbon). However, by far the most commonly used methods are either water or gas atomisation.

Others

Solid State Reduction
Electrolysis
Electrodeposition
Mechanical Comminution

As described above, the process of the invention may be carried out using some form of particle accelerator, such as that described in International Patent Application No PCT/EP00/09960 and using the operational parameters described in this Application, or by means of manual treatment of a surface.

The invention is not limited to the embodiments hereinbefore described which may be varied in both construction and process step without departing from the invention.

The invention claimed is:

1. A process for blasting a surface to remove a coating from the surface, the process being of the type which employs an erasing agent comprising a plurality of particles, the process comprising the step of propelling the erasing agent against the surface such that at least some of the particles roll along at least a portion of the surface, wherein an angle of incidence of the particles and the surface is between 0° and 60°, wherein the particles are generally round and have an irregular surface configuration to effect a rolling movement along the surface such that the particles rub and absorb the coating from the surface, and wherein the particles have an average maximum diameter of between 30 and 1000 microns, wherein each particle comprise a precipitate or agglomerate of an insoluble alkali metal carbonate.

2. A process as claimed in claim 1 for use with dental applications such as teeth whitening, plaque removal and general cleaning or polishing of the teeth, buccal cavity and prosthetic parts such as crowns, bridges and complete or partial dentures.

3. A process as claimed in claim 1 in which the particles comprise a precipitate or agglomerate of an insoluble calcium carbonate.

4. A process as claimed in claim 1 in which the erasing agent is substantially non-aqueous.

* * * * *